United States Patent [19]

Matthews et al.

[11] Patent Number: 4,606,645

[45] Date of Patent: Aug. 19, 1986

[54] METHOD FOR DETERMINING LOCALIZED FIBER ANGLE IN A THREE DIMENSIONAL FIBROUS MATERIAL

[75] Inventors: Peter C. Matthews, Poole, England; Jon F. Soest, Sumner, Wash.

[73] Assignee: Weyerhaeuser Company, Tacoma, Wash.

[21] Appl. No.: 665,609

[22] Filed: Oct. 29, 1984

[51] Int. Cl.[4] ............................................. G01N 21/47
[52] U.S. Cl. .................................... 356/446; 162/198; 250/562; 250/572; 356/237; 356/445
[58] Field of Search ...................... 356/445–448, 356/371, 237; 250/563, 559, 571, 560–562, 572; 83/72; 162/263, 198

[56] References Cited

U.S. PATENT DOCUMENTS

| | | | |
|---|---|---|---|
| 3,471,702 | 10/1969 | Van Veld | 250/219 |
| 3,574,470 | 4/1971 | Vukelich et al. | 356/446 |
| 3,591,291 | 7/1971 | Greer et al. | 356/371 |
| 3,694,658 | 9/1972 | Watson et al. | 250/219 |
| 3,976,384 | 8/1976 | Matthews et al. | 356/431 |
| 3,983,403 | 9/1976 | Dahlstrom et al. | 250/560 |
| 4,092,068 | 5/1978 | Lucas et al. | 356/73 |
| 4,097,160 | 6/1978 | Yataki et al. | 250/563 X |
| 4,149,089 | 4/1979 | Idelsohn et al. | 250/563 |
| 4,184,175 | 1/1980 | Mullane, Jr. | 358/93 |
| 4,199,261 | 4/1980 | Tidd et al. | 356/448 |
| 4,274,288 | 6/1981 | Tittman et al. | 73/602 |
| 4,286,880 | 9/1981 | Young | 356/431 |
| 4,403,294 | 9/1983 | Hamada et al. | 364/507 |
| 4,412,746 | 11/1983 | Yokouchi | 356/446 |
| 4,518,259 | 5/1985 | Ward | 356/446 |

FOREIGN PATENT DOCUMENTS 2499717 8/1982 France .

OTHER PUBLICATIONS

Davis, et al., Def. Pub. T392,008 (1975).

Primary Examiner—Vincent P. McGraw
Assistant Examiner—Robert D. V. Thompson

[57] ABSTRACT

The invention is a method for measuring fiber angle in a fibrous solid material relative to three mutually orthogonal reference axes. It is particularly well suited for measuring diving grain and grain surface angle in wood. The method is based on the measurement of the intensity of reflected light at different azimuthal angles when a beam of light of small diameter is impinged upon the surface. The nature of the specular reflections from a light beam striking the surface of a cylinder serves as a model for the system. A preferred apparatus for practicing the method comprises a light source, which may be a low powered laser, aimed normal to the surface of the fibrous material. A plurality of photosensors lying in a plane normal to the axis of the light beam are placed around the light source to detect the light reflected at various azimuthal angles. When the fibers of the material lie normal to the light beam, reflected light maxima are seen 180° apart at positions normal to the longitudinal axis of the fibers. If the fiber axes in the material are tilted out of normalcy with respect to the incoming light beam, even though the surface of the material is normal, the azimuthal angle between the reflected light maxima decreases as a function of the tilt angle. Various alternative methods include the use of an on-axis photosensor with a multiplexed series of light sources arranged around the axis. These lights may be used simultaneously if they are of different wavelengths and the photosensor employs a beam splitting and filtering system sensitive to each different light source.

45 Claims, 27 Drawing Figures

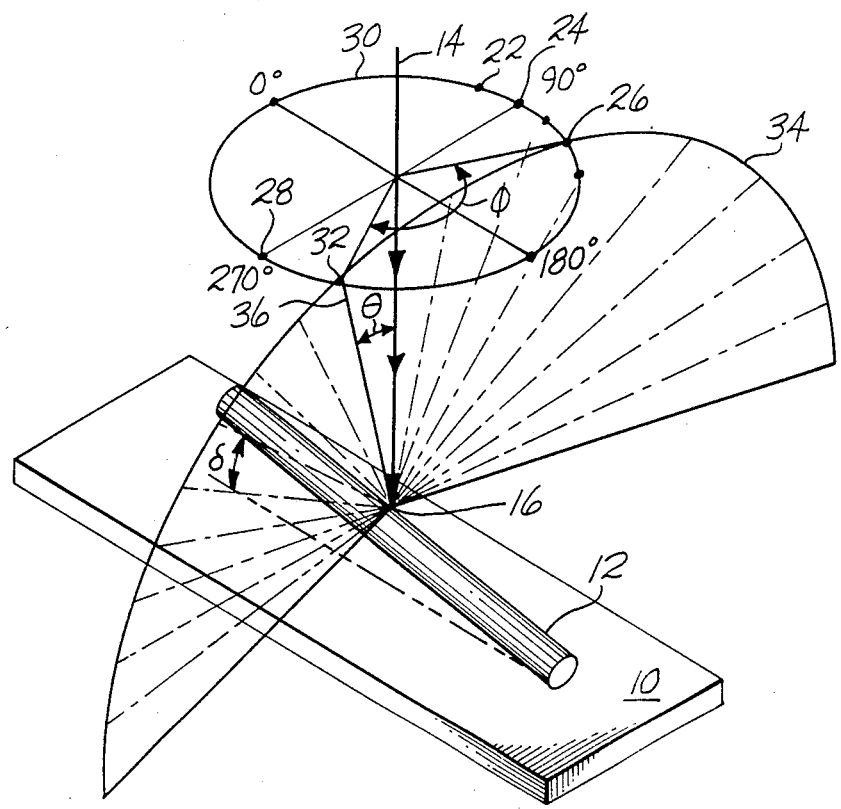
*Fig.*9
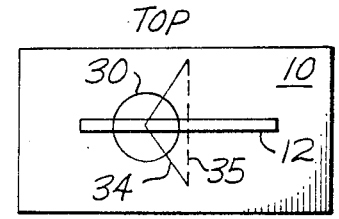
*Fig.*9A
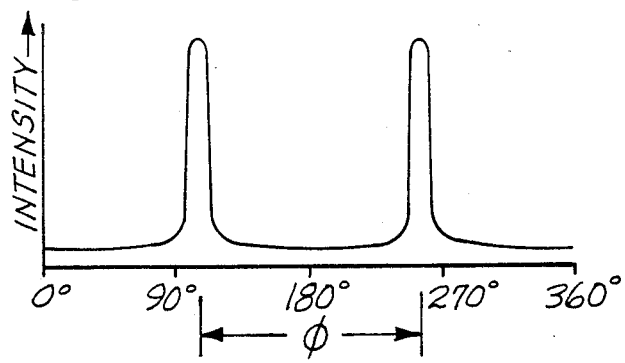
*Fig.*9C
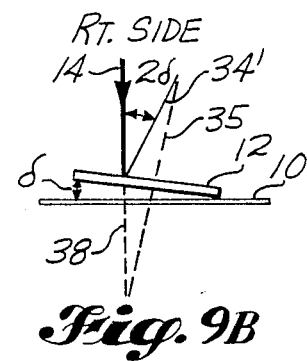
*Fig.*9B

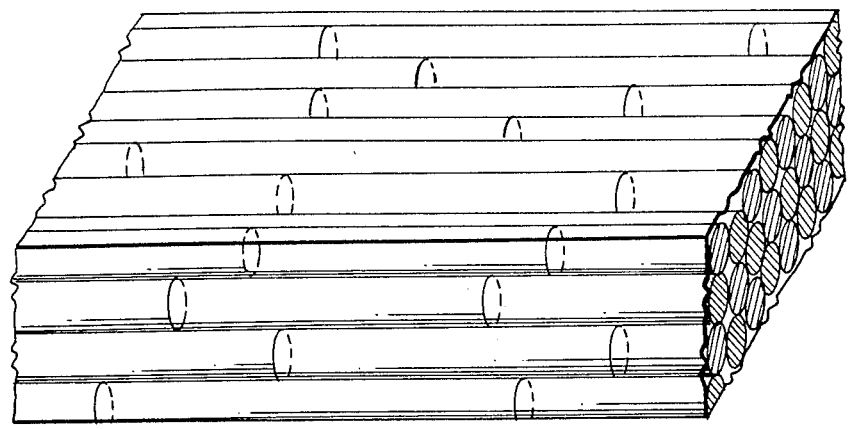
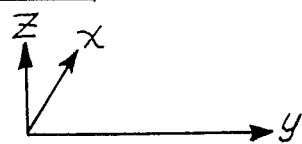
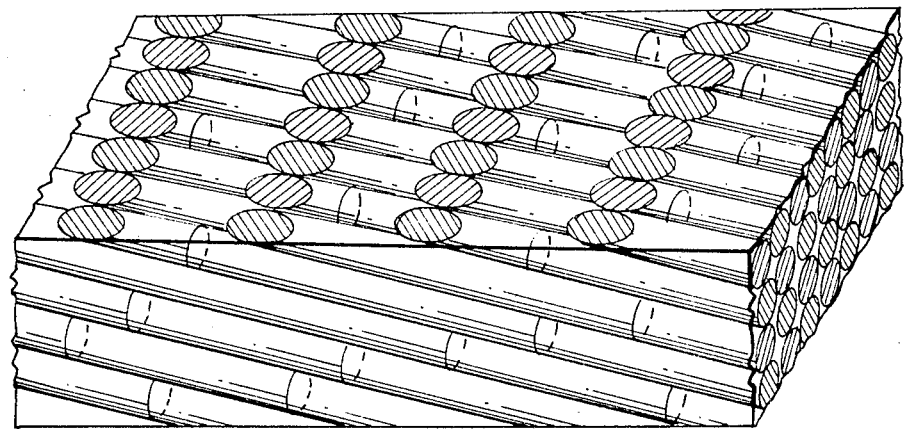
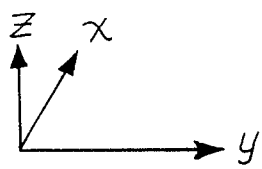

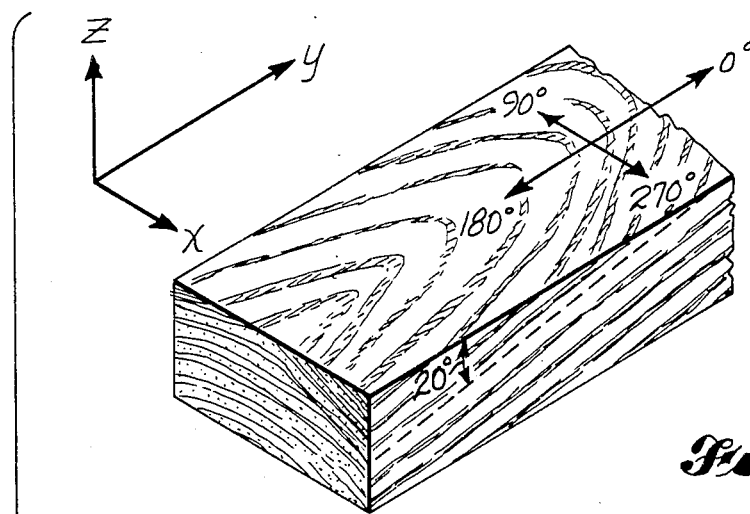
*Fig.*14
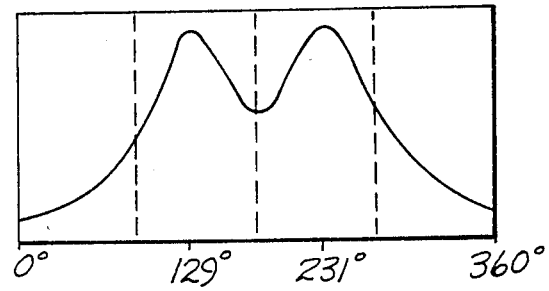
*Fig.*14A
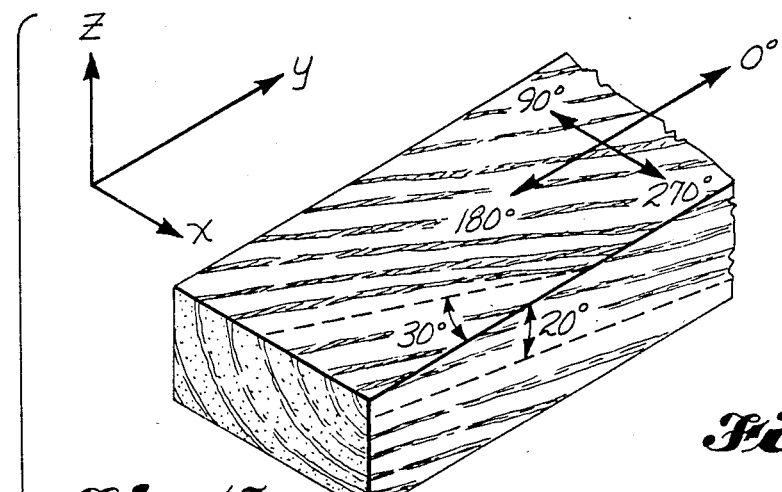
*Fig.*15
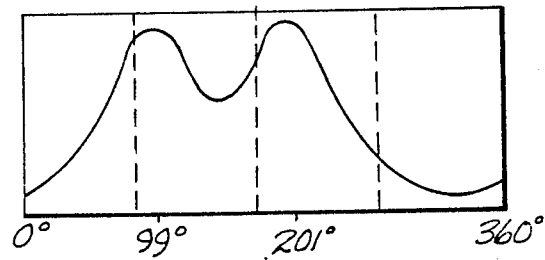
*Fig.*15A U.S. Patent   Aug. 19, 1986   Sheet 9 of 9   4,606,645

METHOD FOR DETERMINING LOCALIZED FIBER ANGLE IN A THREE DIMENSIONAL FIBROUS MATERIAL

BACKGROUND OF THE INVENTION

The present invention is a method for measuring the fiber angle in a solid fibrous material relative to any of three mutually orthogonal reference axes. The method is particularly well adapted for measuring fiber angle in wood and wood products for use in conjunction with an automatic grading or stress rating system.

Wood is a highly anisotropic material composed of bundles of several types of lignocellulosic fibers. The great majority of these fibers are formed generally parallel to the pith or longitudinal axis of the tree. However, growth anomalies can greatly distort this parallelism in localized areas. One such anomaly is twist. This is a situation in which the growing tree lays down fibers in a helical fashion around the pith. A better known anomaly is caused by knots. A knot is caused when a growing tree forms new wood around an existing live or dead branch. A further example is caused by wounds which injure the cambium tissue under the bark. These cause the growing tree to lay down a form of scar tissue in which fiber direction can vary wildly.

Fiber direction, more commonly termed grain direction, has a significant effect upon the appearance and strength of the wood. Many "figured" hardwoods owe their appearance to small scale variations in fiber direction. One example would be the well known "fiddleback" pattern caused by the fibers being laid in a sinuous, rather than linear, pattern. Fiber angle variations are particularly important in wood destined for structural or construction uses. In many uses where stresses tend to induce bending, the allowable load is directly dependent on the uniformity and linearity of the fiber orientation in the member. Ideally, in construction wood, all of the fibers would be parallel to the longest axis of the member. This ideal is at best only approximated in the highest grades of lumber, which are essentially free from defects such as knots. The probable presence to some degree of less readily seen defects, such as those that might be caused by spiral grain, cause allowable stress ratings to be assigned very conservatively within any grade of lumber.

Lumber grading is normally carried out visually, using a well defined set of rules agreed upon throughout the wood products industry. In recent years, some lumber has been machine stress rated in addition to being visually graded. This is normally done automatically in a device that bends the individual pieces of lumber as a plank; i.e., with the load applied to the broadest face. Either a constant load is applied and the deflection measured, or a variable load is applied to achieve a given deflection. In either case, the property calculated is the modulus of elasticity. This value correlates with the flexural strength, also called the modulus of rupture, when the member is used as a joist; i.e., with the load applied to the narrower cross sectional dimension.

Machine stress rating used in conjunction with visual grading has been of considerable value to the user who has applications that have a critical dependence upon the strength of the wood. One such application might be the manufacture of glued laminated beams which frequently serve as major structural members in large buildings. Even so, the forces applied during machine stress rating are far short of those that would generally cause failure and they frequently fail to discriminate against potential weak areas caused by certain types of grain anomalies. One of these anomalies is a major fiber deviation from parallelism with the longitudinal axis. This can occur even in the absence of a knot or similar defect. In particular, the defect known as "cross grain" or "diving grain" is often very difficult or impossible for a grader to see. Diving grain, broadly stated, is the aforementioned phenomenon in which the fiber direction is not parallel to the longitudinal axis of a member, but is either angled upward or downward in reference to the plane defining at least one face of the member, when the member is of rectangular cross section. Diving grain may also be present in wood products having other geometric cross sections, such as circular.

Diving grain is always associated with knots but it can also be present without any other visible defects being present. It must be remembered that a typical sawlog is a truncated cone due to the natural taper present in most logs. Sawmill limitations which prevent sawing lumber parallel to the outer surface will produce diving grain to some degree. The ability to detect and measure it by a scanning system opens broader opportunities for more accurate stress rating as well as more comprehensive types of machine grading.

The concept of optical grading of wood is in itself not new. As one example, U.S. Pat. No. 3,976,384 to Matthews et al., describes an optical system concerned with the detection of defects such as knots, blue stain, and certain types of rot. These inventors "inject" light into the surface of wood at one point and measure the emerging light at an adjacent point. They have noted that in clear (defect free) wood, light traveling across the grain is attenuated by a factor almost 50 times greater than light traveling along the grain. The method senses surface fiber direction changes on the plane of the face being measured but is unable to satisfactorily detect diving grain or accurately measure surface grain direction. In addition, it had been found to be unsuitable for use on the wood of deciduous, or so-called "hardwood", species.

In French Pat. No. 2,499,717, a wood surface is illuminated with a polarized beam of light having the plane of polarization either parallel to or perpendicular to the longitudinal axis of the piece of wood. The light reflected from a piece of sound wood is only partially depolarized while light reflected from a knot is almost totally depolarized.

Davis et al., in U.S. Defensive Publication No. T932,008, disclose an optical system for measuring surface fiber direction in a moving web structure. These authors note that when collimated light is projected on a fibrous web, the light will be reflected with greatest intensity perpendicular to the fiber axes. To take advantage of this effect they illuminate a spot on the moving surface and measure the reflected light in the machine direction, in the cross machine direction, and at 45° to the machine direction. A spot of collimated light is projected vertically onto the surface with the sensors being located at an angle of 45° from the vertical. The degree of illumination is controlled to maintain a constant reflectance. Reflectance values measured along and across the machine direction can be used to determine the average orientation of the fiber.

The three systems just described are useful for detecting, and in one case measuring, deviations in surface fiber from a longitudinal orientation. Stated differently, they are limited to describing the fiber condition on a planar surface but unable to describe fiber orientation with respect to the three axes of a solid material. As an example, in wood they could detect and measure fiber surface angle only but would be unable to supply any information as to whether or not diving grain was present.

Certain other investigators have devised apparatus suitable for discovery of subsurface anomalies in translucent materials. Mullane, Jr., in U.S. Pat. No. 4,184,175, describes equipment useful for detection of subsurface flaws in teeth. Vukelich et al., U.S. Pat. No. 3,574,470, describe void detecting apparatus for a material such as polyurethane foam. Light is beamed into the material and the reflectance is measured. Areas having internal voids will reflect less light. Young, in U.S. Pat. No. 4,286,880, and Idelsohn, in U.S. Pat. No. 4,149,089, describe flaw detection systems for wood. Each of these systems also requires the presence of a human inspector who works in cooperation with the scanning system.

Other optical scanners are shown in patents to Hamada et al., U.S. Pat. No. 4,403,294 and Watson et al., U.S. Pat. No. 3,694,658.

Lucas et al., in U.S. Pat. No. 4,092,068, describe a scanner for determination of paper surface roughness and the detection of dirt. The device is especially sensitive to dirt particles because their reflectivity is very different from that of the paper. Lucas illuminates a circle from about 0.1 to 0.2 mm in diameter and uses two angularly spaced detectors to measure reflected light. Greer et al., in U.S. Pat. No. 3,591,291, and Tittmann et al., U.S. Pat. No. 4,274,288, teach methods for measuring the depth and frequency of surface flaws in objects.

Dahlström et al., in U.S. Pat. No. 3,983,403, teach a scanner system useful for detecting and measuring wane in lumber. In an invention that is somewhat related to the disclosure of Davis et al., Van Veld, in U.S. Pat. No. 3,471,702, notes that the ratio between diffuse and specularly reflected light correlates with the bulk of a strand of yarn. One detector is focused along the line of specular reflection and a second detector is located $17\frac{1}{2}°$ off this axis.

While all of the above scanning systems are undoubtedly useful for the purposes described, none of them have the ability to "see into" a fibrous three dimensional material so as to measure fiber angle with respect to all three axes. As will henceforth be described, the present invention has overcome this major limitation.

SUMMARY OF THE INVENTION

The present invention relates to measuring fiber angle in a fibrous solid material relative to three mutually orthogonal reference axes. The material being measured need not be transparent or translucent as long as the fibers are present at a surface in relatively undisturbed form. The method is particularly useful for measuring fiber orientation in wood. It can be used equally well with other fibrous or fiber-containing materials such as fiber reinforced plastics.

The method is based upon the type of reflections noted when a beam of light, preferably collimated and which may be coherent light, is impinged upon the surface of a shape which can approximate a cylinder. This is best described by using a cylinder with a semi-matte surface as a model. When a beam of light of finite diameter impinges on the surface, the reflected light will have both specular and diffuse components. The relative magnitude of the specular and diffuse reflections will depend on the nature of the particular surface. The viewing area for reflected light should be considered as a hemisphere whose polar axis is coincident with the incident light beam. Reflected light striking the viewing area will be normally be sampled at a sufficient number of locations so that the nature of the complex reflection can be determined. One way to sample the reflected light is to locate a plurality of photosensors around the circle described where a reference plane intersecting the polar axis cuts through the hemisphere. Stated differently, the polar axis may not be a line lying on this plane or on a plane parallel to the reference plane. It is a matter of convenience if the reference plane is normal to the polar axis.

When the incident beam strikes the surface of a cylinder radially, normal to the longitudinal axis, the specular component of the reflection will be essentially two dimensional and can be described as fan-shaped, or as the upper half of a circle lying in a plane normal to and centered on the longitudinal axis of the cylinder. This component will be represented on the viewing hemisphere as an arc of light falling from equator to equator along polar meridans. However, when the incident beam is not normal to the longitudinal axis, the specular component of the reflection becomes three dimensional and can be described as a cone of light, with the longitudinal axis of the cylinder and cone being coincident. This cone of light will, in effect, be "tilted forward" (or rearward) dependent upon the angle between the incident beam and the longitudinal axis of the cylinder. Its intersection on the viewing hemisphere will no longer fall along polar meridians. As the incident angle increases, the included angle of the light cone will decrease.

In the first case, when the incident beam strikes the cylinder normal to the longitudinal axis, a ring of photosensors lying around a circle with the polar axis at its center will "see" specular reflected light at only two points. These lie along a diameter which, when projected onto the plane containing the longitudinal axis of the cylinder, will be normal to that axis. The points at which light is detected will be separated by an azimuthal angle of 180°. In the second case, when the incident beam is not normal to the longitudinal axis of the cylinder, the azimuthal angle between these points will be less than 180°. By noting the position of the points at which the specular component of the reflection intersects the circle of detectors, assuming that other parameters of the system are known, both the angle of inclination and the orientation of the longitudinal axis of the cylinder can be measured.

In this model, and in practical applications using wood, the reflected light will also have a diffuse component imposed upon and additive to the specular component. The diffuse component is reflected at all angles. This causes additional detectors around the circle to "see" light with the effect that the sharpness of the specular maxima is somewhat decreased.

A knowledge of the above phenomena makes it possible to measure fiber angle within a solid material. This material can be of any geometric shape that can be defined in relationship to three arbitrarily assigned, mutually orthogonal reference axes. One of these axes projecting from a surface into space will be designated as the polar axis and a second axis will be named the reference axis. For convenience, the origin point of the axes may be on the surface of the material. The polar axis will usually be normal to the surface being investigated and the reference axis may be the longitudinal axis. The area on the surface illuminated with the incident beam of light should include the origin point.

In one method of the present invention, at least four photosensing receptors are located in positions to view the illuminated area. At least one photosensor should lie in each quadrant surrounding the polar axis. These quadrants may be arbitrarily defined. They will usually be divided by the reference axis and the third axis, but this is not essential. Light reflected from the illuminated area is then sensed by the photosensors. From a knowledge of the relative light intensities measured by the photosensors, the azimuthal angular positions are estimated for the points of maximum intensity of the reflected light, relative to the reference axis. A set of simple trigonometric algorithms will relate the azimuthal angular positions of the reflected light maxima to the fiber angle relative to all three axes.

Conveniently, the photosensors are located in a plane normal to the polar axis and, preferably, lie at essentially equiangular positions around a circle whose center is located at the polar axis. At least four photosensors are required. However, larger numbers improve the resolution and enable more accurate fiber angle determinations. A minimum of eight photosensors is preferred.

The incident light beam may be white or monochromatic light focused by normal optical means or it may be coherent light delivered from a low power laser. Preferably the incident light beam is collimated; i.e. the edges of the beam are essentially parallel or diverge at a very low angle. In any case, the area illuminated should have a diameter at least ten times the average fiber diameter of the fibrous substance being measured. When the material being measured is wood, illuminated areas ranging between about 0.5 to 4 mm in diameter have proved to be very satisfactory. The illuminated area need not be perfectly circular. In fact, a circular area is achieved only when the light beam follows a path normal to an essentially flat surface.

As one alternative method, at least one photosensor may be used in a position to view the origin point of the axes. This point can then be sequentially illuminated with a beam of light originating from at least four positions around the polar axis. At least one of these positions should lie in each of the quadrants surrounding the polar axis. Determination of fiber angle is carried out as explained above. It will be evident to those skilled in the art that the positions of light source and receptor can be interchanged as desired or convenient without affecting the results obtained or the method of calculating fiber angle. It is the intention of the inventors that the method should be broadly construed so as to include either arrangement.

As another alternative method, the area around the origin point can be illuminated with at least four light sources arranged as described above. Each light source will have a different wavelength that may range from the infrared through ultraviolet. Generally wavelengths from the longer end of the spectrum are preferred. The illumination sources can be used in sequential fashion, as described above, or simultaneously. Reflected light is directed through a beamsplitting means to individual photosensors, each uniquely sensitive to the radiation from one of the sources. Appropriate state-of-the-art normalizing circuitry may be provided so that each light source and photosensing means is placed on a comparable basis.

It is an object of the present invention to provide a nondestructive method of measuring the fiber angle in a three dimensional fibrous material relative to three mutually orthogonal reference axes.

It is another object to measure the fiber angle in a solid material by analyzing the diffuse and specular reflections from an area on the surface of the material illuminated with an incident beam of light.

It is a further object to provide a method of measuring the fiber angle in wood relative to three mutually orthogonal reference axes.

It is yet another object to provide a method for determination and measurement of fiber anomalies in wood that could have an adverse effect upon its strength.

It is still a further object to provide a method useful for defining defects in wood that may not be readily apparent from visual inspection.

These and many other objects will become readily apparent to those skilled in the art upon reading the following detailed description and by reference to the drawings.

BRIEF DESCRIPTION OF THE DRAWINGS

FIG. 9 is a perspective view similar to that of FIG. 8 in which the incident light beam is not normal to the longitudinal axis of the cylinder.

FIG. 9A is a top plan view of the configuration shown in FIG. 9.

FIG. 9B is a side elevation of the configuration shown in FIG. 9.

FIG. 9C is an azimuthal scan of reflected specular light intensity from the configuration shown in FIG. 9.

FIG. 10 is a representation of a solid fibrous material in which the fibers are modeled as end-to-end cylinders lying parallel to the major surfaces.

FIG. 11 is a model similar to FIG. 9 in which the fibers are shown in a diving relationship within the y-z plane.

FIG. 14 is an example of a piece of wood having grain diving at 20° to the y axis when viewed from the y-z plane.

FIG. 14A is an azimuthal scan of light reflected from the major surface of the wood shown in FIG. 14.

FIG. 15 is an example of a piece of wood having both diving grain and surface grain angled with respect to the y axis.

FIG. 15A is an azimuthal scan of the intensity of light reflected from the major surface of the wood represented in FIG. 15.

DESCRIPTION OF THE PREFERRED EMBODIMENTS

Figure 1:
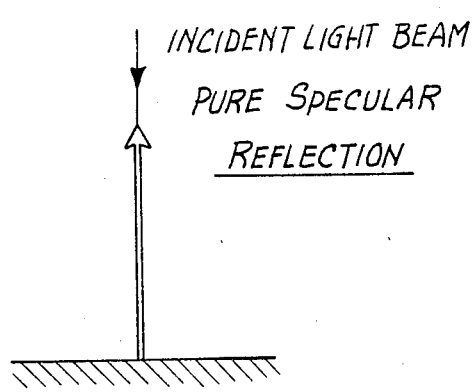
FIG. 1 indicates the path of a reflected light beam when a collimated beam is incident normal to a purely specular reflecting surface.

The method of operation of the present invention is best conceptualized by reference to a series of simplified models. FIG. 1 shows the type of reflection obtained when a beam of light strikes a planar, mirror-like surface at an angle normal to the the surface. In this case, the reflected beam is returned exactly along the axis of the incident beam. A reflection of this type is achieved only from a high quality surface, such as a first surface mirror.

Figure 2:
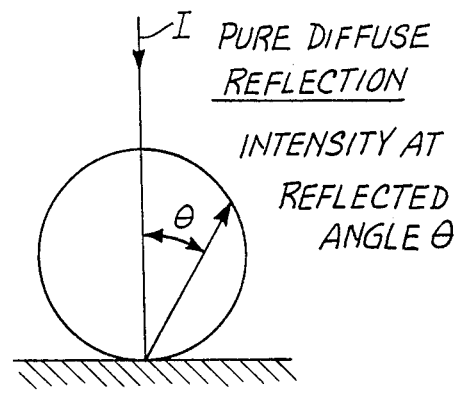
FIG. 2 is a drawing of the reflection intensity as a function of polar angle, taken at one azimuthal angle, when the surface produces a diffuse or Lambertian reflection.

FIG. 2 represents the reflection from a matte surface which does not reflect any specular component. The circle representing reflection intensity is actually a crosssectional representation at a given azimuthal angle.

Figure 3:
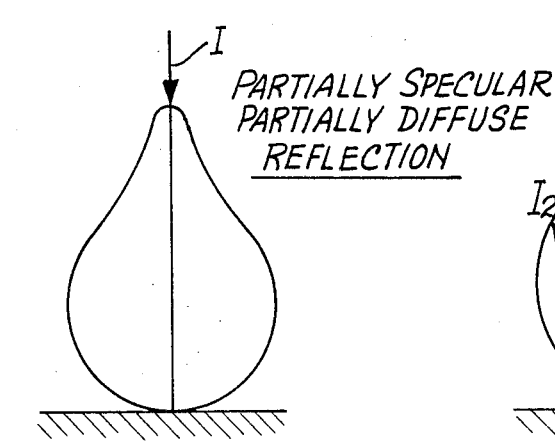
FIG. 3 is similar to FIG. 2; however, here the surface produces a partially specular, partially diffuse reflection.

FIG. 3 shows a more typical reflection which contains both specular and diffuse components. Again, the pear-shaped crosssection is taken at a given azimuthal angle.

The reflections represented from surfaces shown in FIGS. 1 through 3 are actually figures of rotation; i.e., they are identical at any azimuthal angle.

Figure 4:
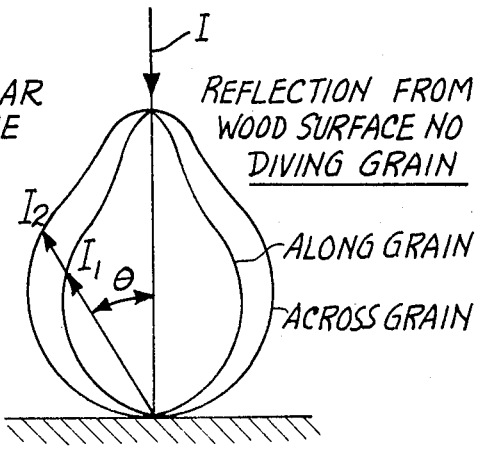
FIG. 4 shows typical reflection intensities from a defect-free wood surface, taken along and across the grain direction.

FIG. 4 represents the reflections from a planed wood surface. The crosssectional representations are no longer figures of rotation but are asymmetrical. Light measured at a given polar angle $\theta$ will be of greater intensity when measured across the grain direction than when measured along the grain direction.

Figure 5:
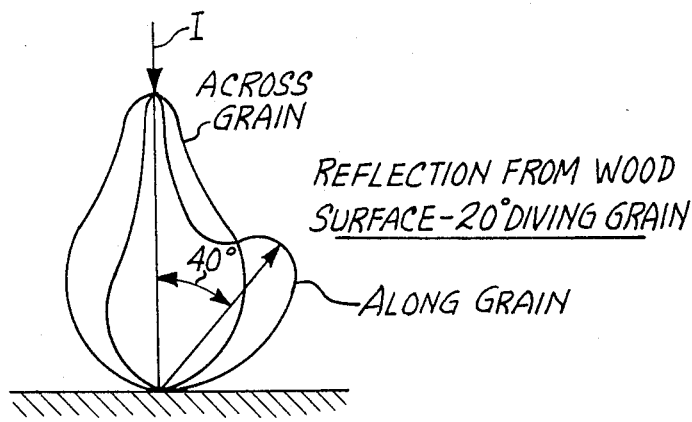
FIG. 5 is similar to FIG. 4 showing reflections from a wood surface in which the fibers dive at a 20° angle to the surface.
Figure 6:
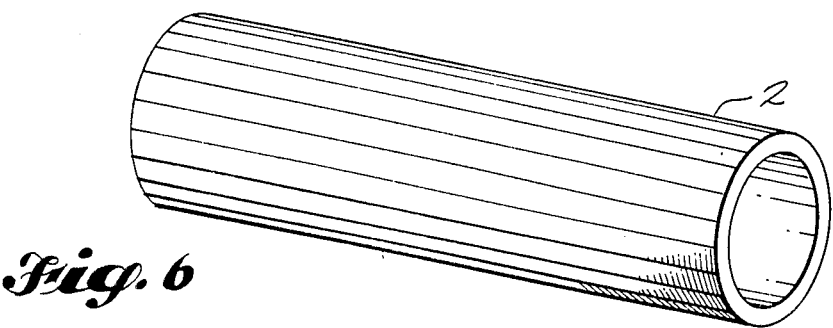
FIG. 6 is a representation of a cylinder modeled as a multifaceted shape.

FIG. 5 shows typical polar reflections from wood having a fiber angle diving 20° below the surface plane. The reflection intensity measured across the grain remains symmetrical about the polar axis. However, the along grain reflection becomes asymmetrical and shows a lobe peaking at 40° from the polar axis. This lobe is present at an angle which is twice that of the reflecting surface, both being measured from the polar axis.

While it is quite possible to make polar scans of the types shown in FIGS. 1 through 5, this method is usually inconvenient except under some laboratory conditions. An alternative method employing azimuthal scans is preferred because of its greater simplicity. This comprises locating an array of photosensors around the polar axis in positions where they can view the area illuminated by the incident beam of light. A minimum of four photosensors are required and at least one must lie in each quadrant surrounding the polar axis. The position of these quadrants can be arbitrarily defined; i.e., they need not be divided by the longitudinal axis, although this situation is generally preferred. Preferably, at least eight photosensors will be present. While not essential, it is usually more convenient for them to be arranged around a circle whose center is located at the polar axis and which lies in a plane normal to the polar axis. Resolution of the curve defining the reflected light intensity is improved as the number of photosensors increases.

Figure 7:
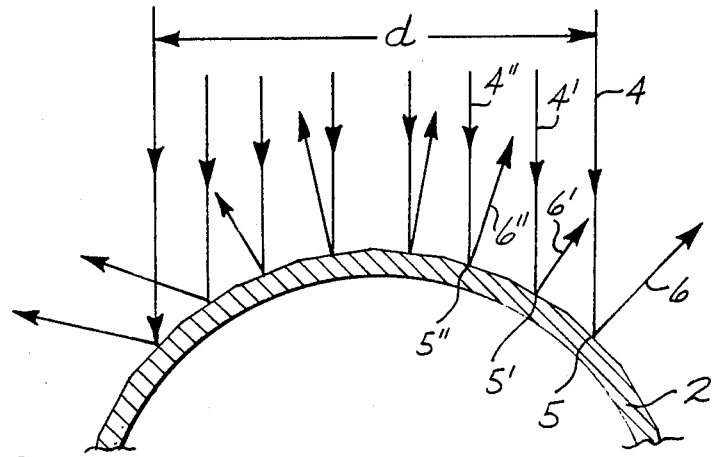
FIG. 7 is a partial cross section of the shape shown in FIG. 6 showing specular components of the reflection pattern from a normal incident beam of light.
Figure 8:
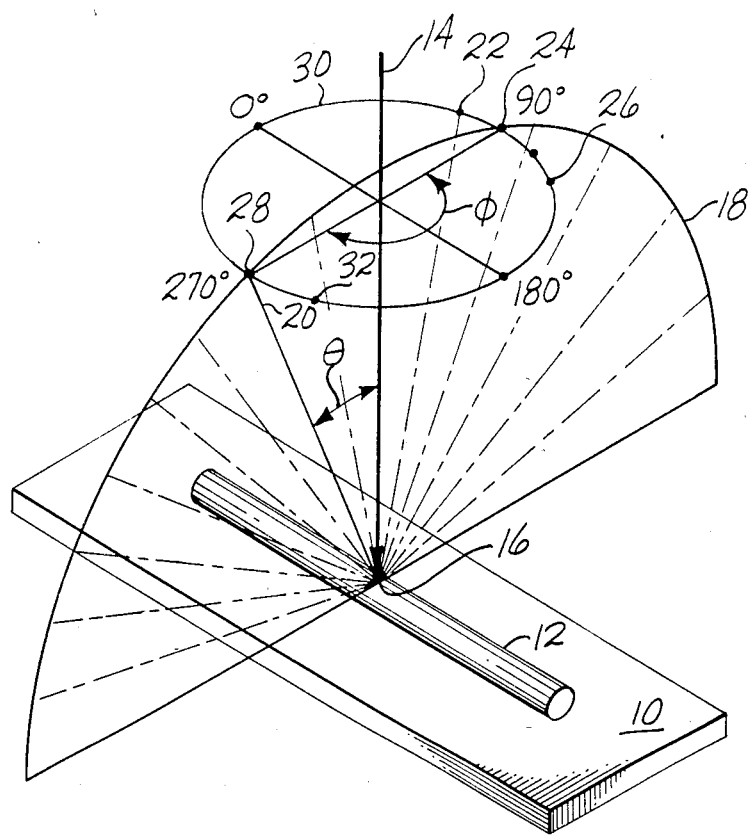
FIG. 8 is a perspective view of the specular reflection pattern when an incident light beam strikes a cylinder at an angle normal to the longitudinal axis of a cylinder

In order to better understand the present invention, it is useful to consider how an incident light beam normal to the longitudinal axis of a cylinder is reflected. For simplification, the cylinder is best conceived as having a polygonal cross section. FIG. 7 shows a geometric shape suitable as a model. A cross section of the model shape, shown at 2 in FIG. 7A, is being illuminated by an incoming collimated light beam 4 of diameter d. This incoming beam may be considered as a bundle of parallel rays 4', 4", etc. which strike facets 5, 5', 5". Specular reflections are sent along paths 6, 6', 6", etc. As the number of facets on the model shape becomes infinite, its cross section becomes circular and the specular reflection will be a solid fan of light emanating from the illuminated surface. This is shown in perspective view in FIG. 8. A cylinder 12 lying on a reference plane 10 is illuminated by an incident light beam 14 which forms a lighted area 16 having a finite diameter. The specular component of the reflection forms a planar fan of light 18. Incident light beam 14 lies on the polar axis of the system. A ring of photosensors, only some of which are numbered at 22, 24, 26, 28, are located around a circle whose center is at the polar axis and which lies on a plane parallel to reference plane 10. The specular component of light fan 18 will be "seen" or sensed only by the two photosensors 24, 28. These lie at opposite ends of a diameter of circle 30 and thus are separated by an azimuthal angle of 180°. If projected down on reference plane 10, the diameter would lie transversely normal to the longitudinal axis of cylinder 12. The angle $\theta$ between returning light ray 20 and incident light beam 14 defines the polar angle between the receptors and incident light.

Figure 8A:
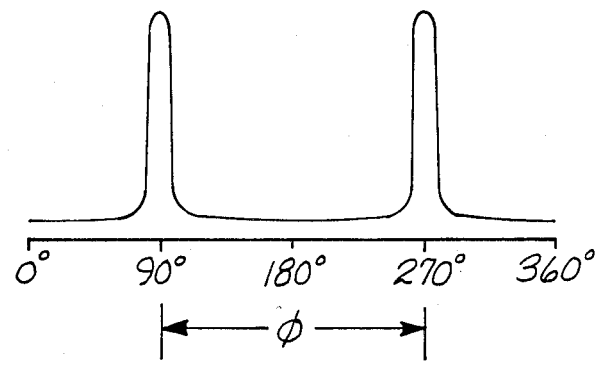
FIG. 8A is an azimuthal scan of reflected specular light intensity measured by a ring of photosensors located around the incident light beam of FIG. 8.

FIG. 8A shows an azimuthal scan of the output from the ring of photosensors with the peaks corresponding to the positions of photosensors 24 and 28.

In FIG. 9, one end of the cylinder 12 has been raised from reference plane 10 by an angle $\delta$. Now, instead of a planar fan, the specular component of the reflected light is in the form of a cone 34. This cone has an included angle and a forward inclination from the polar axis which are both dependent upon angle $\delta$. The geometry of this example can perhaps be better visualized by reference to FIGS. 9A and 9B. Line 35 is drawn arbitrarily for sake of visualization and does not exist in reality because the cone continues to project out into space. It it worthy of note that the longitudinal axes of the light cone and cylinder 12 are coaxial. The light cone is more properly described as a half cone because the lower portion that would fall below the cylinder does not exist in reality because it is in the shadow area. Surface 38 of this imaginary portion is seen in FIG. 9B to lie along a projection of the incident ray. As would be expected of the reflection from a mirror-like surface, line 34' in FIG. 9B is at an angle of 2δ from incident ray 14.

Looking back at FIG. 9, the specular reflection now intersects the circle 30 of photosensors at points 26 and 32. Here, the included azimuthal angle Φ becomes less than 180°. This is shown also in the light intensity output scan in FIG. 9C.

It now is apparent that for a single cylinder under the conditions described, a knowledge of the position of the specular peaks can define the position of the axis of the cylinder in three dimensions. The dive angle δ can be calculated by the following formula:

$$\tan \delta = \tan \theta/2 \cdot \cos (\Phi_1 - \Phi_2)/2$$

where $\Phi_1$ and $\Phi_2$ are the light intensity maxima points and $\theta$ is the angle between the polar axis and rays extending from the illuminated spot to the photo sensors.

When making actual measurements on materials, the diffuse component of the reflections must be taken into account. This will be additive with the specular component as will be readily apparent in azimuthal scans. In the idealized systems just described, this serves to broaden out the sharp peaks attributed to the specular component but it does not significantly change their position. However, with the diffuse component present, most or all of the photosensors located around circle 30 would now show an output signal which would also be dependent on dive angle δ.

Quite surprisingly, the principle just discussed using single reflecting cylinders as models is equally valid for fibrous solid materials which can be modeled as bundles of cylinders. For example, wood having no fiber direction deviations from parallelism with the longitudinal y axis can be represented as shown in FIG. 10. This system is equivalent to that represented in FIG. 8. A model for wood having diving grain is shown in FIG. 11. This will behave similarly to the system modeled in FIG. 9.

Figure 12:
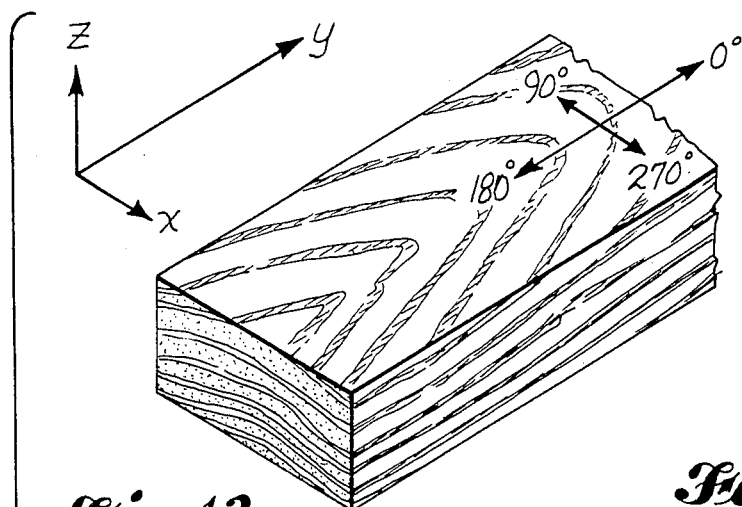
FIG. 12 is an example of a straight grained, defect-free piece of wood.
Figure 12A:
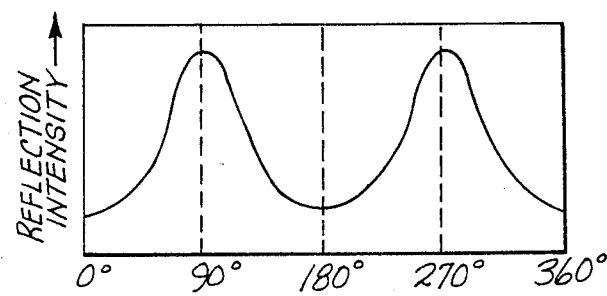
FIG. 12A is an azimuthal scan of the intensity of light reflected from the major surface of the wood of FIG. 12.

A block of wood having its fiber direction essentially parallel to the longitudinal y axis is shown in FIG. 12. When illuminated as in FIG. 8 or 9, it will produce a reflectance pattern as shown in FIG. 12A. It will be immediately apparent that this is identical in general type to the scan shown in FIG. 8A.

Figure 13:
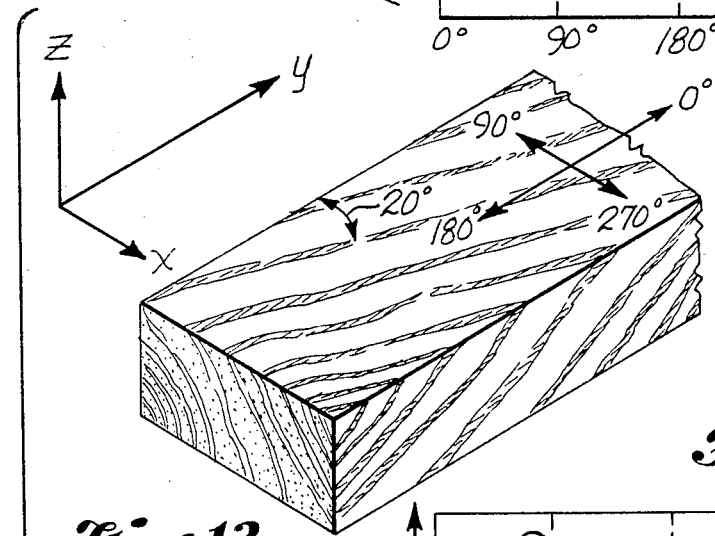
FIG. 13 is an example of a piece of wood having a surface grain running at a 20° angle to the y axis.
Figure 13A:
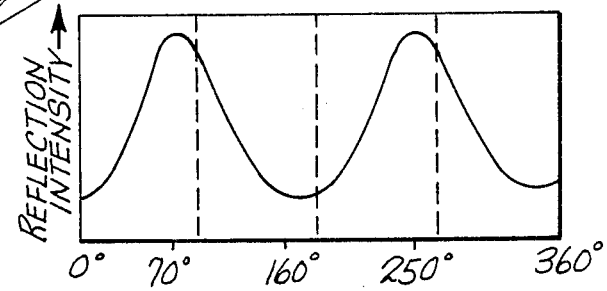
FIG. 13A is an azimuthal scan of the intensity of light reflected from the major surface of the wood of FIG. 13.

FIG. 13 is an example of wood having angled surface grain. This grain is not diving with respect to the y axis when viewed on the y-z plane. Fiber direction does deviate by 20° from the y axis when viewed on the x-y plane. The light intensity scan, shown in FIG. 13A, is similar to that in FIG. 12A. However, the maxima in FIG. 13A are shifted by 20° to lower angles than those of FIG. 12A. Thus, the present method is also useful for measuring fiber angle in the surface plane, even when no dive into the wood is present.

FIG. 14 is an example of showing 20° dive from the y axis when viewed on the y-z plane. Surface angle appears parallel to the y axis when viewed on the x-y plane. The reflected light scan, shown in FIG. 14A, is similar to that produced by the inclined cylinder as shown in FIG. 9C. In all of FIGS. 12 through 15 it is assumed that the angle θ (the angle between the incoming beam along the z-axis and rays extending from the illuminated spot to the photosensors), is 60°.

FIG. 15 shows a more complex situation in which wood has both angled surface grain and diving grain. Surface grain is angled 30° from the longitudinal y axis with 20° of dive. The light intensity scan is shown in FIG. 15A. The angle between the intensity maxima, is 102°, the same as shwon in the scan in FIG. 14A for a similar diving grain angle. In the scan of FIG. 15A the maxima are displaced to the left by 30° due to the angled surface grain. Thus, both components can readily be determined from a single scan. If it is desired to obtain the total fiber angle in space from the y axis the vector sum of the surface angle and dive angle can be readily calculated by the law of cosines formula:

$$\cos (\text{total angle}) = \cos (\text{dive angle}) \times \cos (\text{surface angle})$$

When measuring the fiber angle, or grain direction, of wood, it is preferable to scan a surface which has been planed or sawn. Sanded surfaces usually have considerable surface fiber distrubance which in some cases may reduce the accuracy of grain angle measurement.

Figure 16:
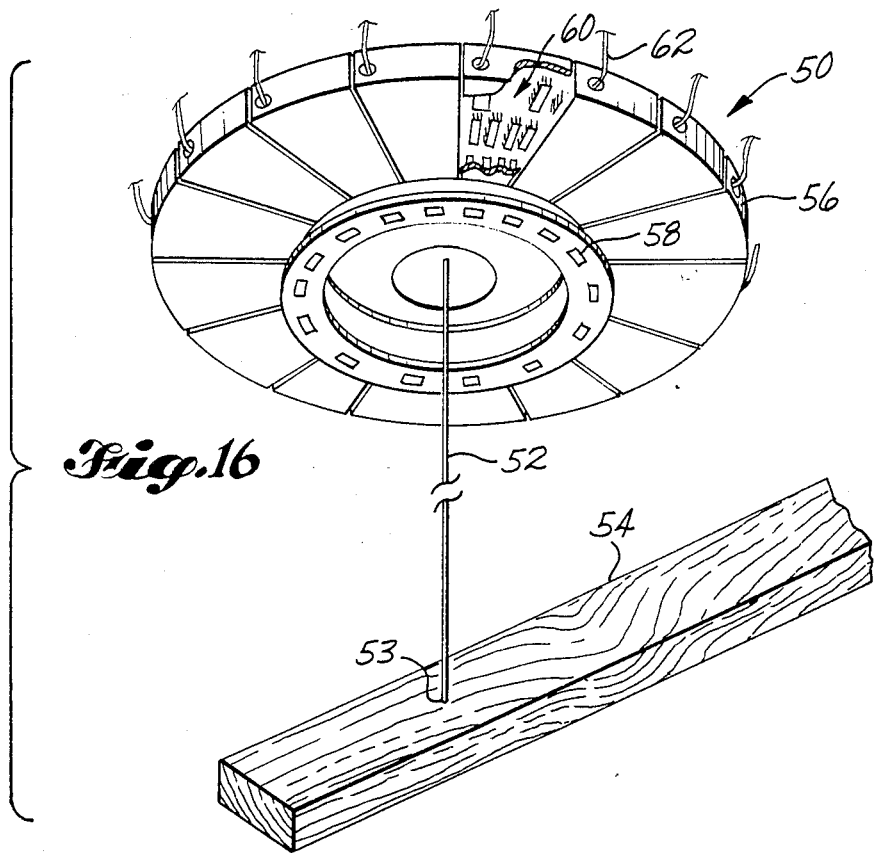
FIG. 16 shows one arrangement of a system for illumination and photosensing reflected light.

FIG. 16 is a representation of an actual scanning head used for the measurement of grain angle in wood. The head, generally indicated at 50, comprises a low power helium neon laser, not shown, which sends a continuous beam 52 impinging at 53 upon the surface of a wooden member 54. Light reflected from the wooden member is received by sixteen photo sensor modules 56 located 22½° apart. Only one module is numbered. These contain one or more photo diodes or other types of light sensitive devices 58 and associated circuitry 60. It is convenient to scan the photo diodes by a multiplexing circuit and feed the outputs directly to a computer input through leads 62. The circuitry may include means for normalizing the photosensors; i.e., ensuring that they will give uniform output for a given light intensity.

Figure 17:
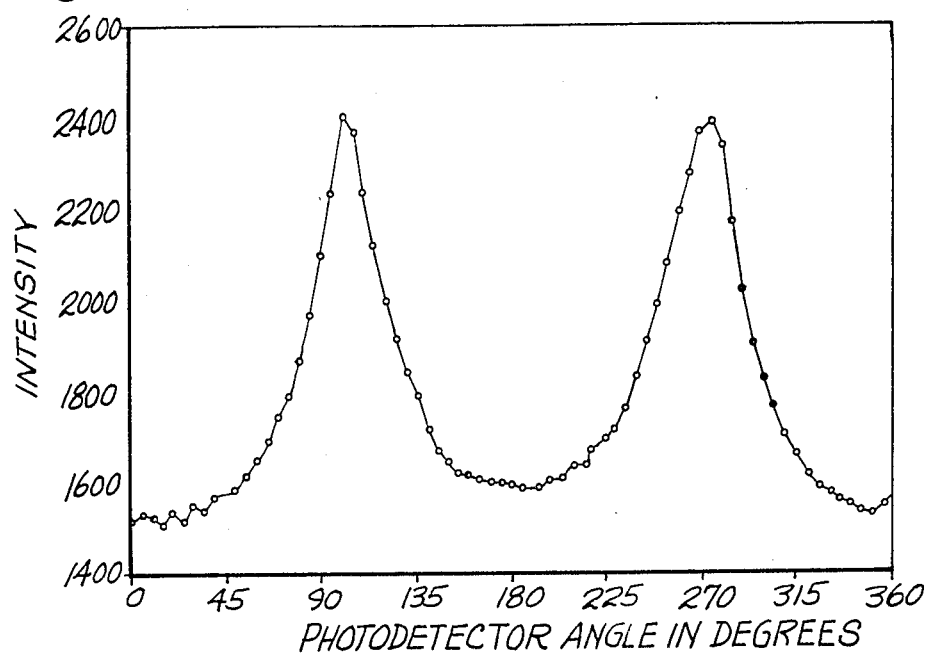
FIG. 17 is an actual curve of light intensity reflected from a wood surface using photo detectors placed every 5° of azimuthal angle.

FIG. 17 is an actual light intensity output curve measured with a detector unit having 72 photo cells, one every 5°. Light intensity maxima are shown at 102° and 274°. The viewing angle ι was 45°. For the area sampled the dive angle was 1.6°, the surface grain angle about 7.8°, and the total angle 8.0°.

Figure 18:
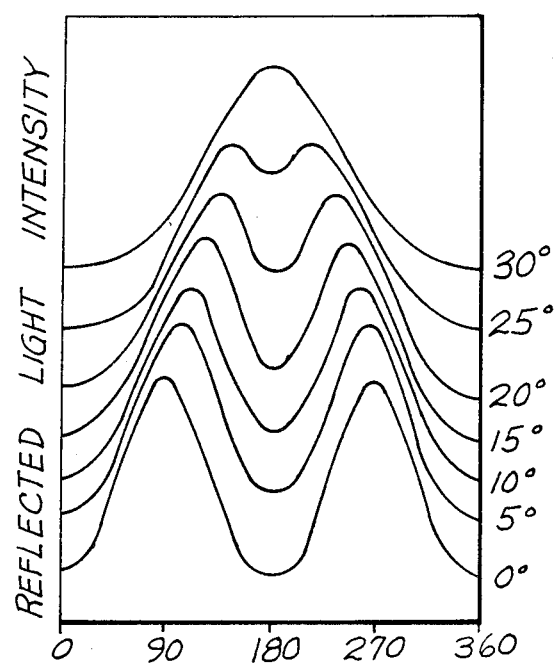
FIG. 18 shows a family of reflected light curves determined from wood samples having varying degrees of diving grain but a common surface grain angle, with detectors located to intercept light reflections at a polar angle of 60° with respect to the incident light beam.

FIG. 18 shows a family of curves demonstrating light intensity scans of wood having different diving grain angles. This indicates dramatically how the intensity maxima move together and finally merge as the dive angle increases to 30°, the maximum that can be detected with the 60° viewing angle used in this instance.

Referring back to FIG. 16, it would be equally satisfactory to use a single photosensor at the location of the laser supplying the incident light beam 52. The light source could be moved to the location 58 and angled so as to illuminate location 53. A single light source could be employed by moving it from position to position. Alternatively, multiple light sources, all focused on the same point, could be used and these could then be multiplexed. Calculations of grain angle would be the same as before.

Figure 19:
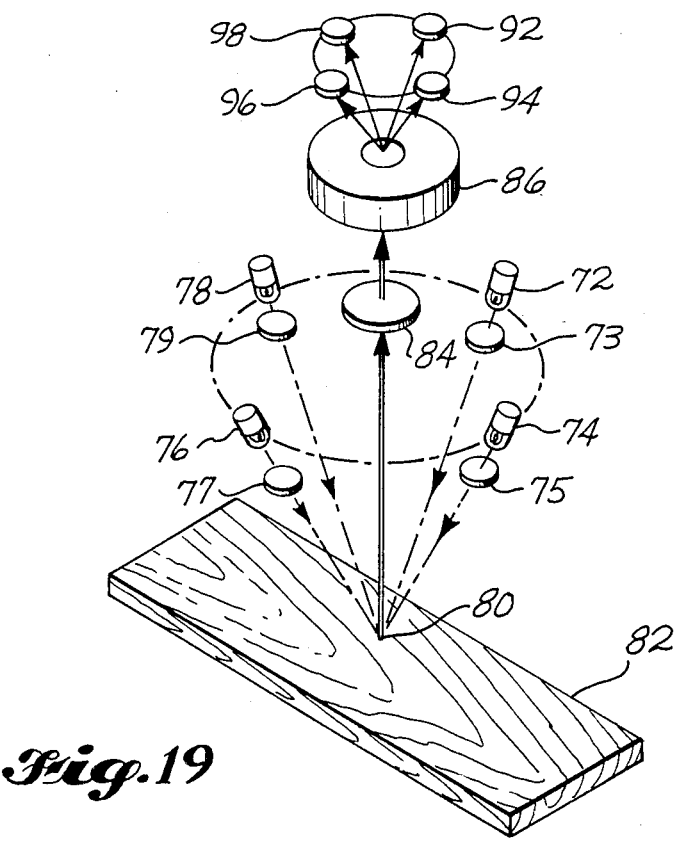
FIG. 19 shows an alternative arrangement of illumination and photosensing components to that shown in FIG. 16.

Another alternative system is shown in FIG. 19. Four light sources 72, 74, 76, and 80 are arranged in a circle around the polar axis with their beams focused on a common point 80. Each of these sources emits light of a different wavelength. This may be accomplished by a number of well known means as, for example, the use of filters 73, 75, 77, and 79. The reflected light is directed through a focusing lens 84 into a beam splitter 86 or similar device from which it is directed to a multiplicity of photosensors 92, 94, 96, and 98. In the example shown, each photosensor is uniquely sensitive to the wavelength from one of the illumination sources. This may be accomplished through the use of filters, not shown, which might be similar in characteristics to filters 73, 75, 77, and 79. The beam splitter may be a prism, diffraction grating, or similar device. An arrangement of this general type is commonly used in color video cameras, as one example. The illumination sources may be multiplexed as above or they may used continuously. Appropriate normalizing circuitry can serve to place both the illumination sources and photosensors on an equivalent operating basis.

The grain angle detection system can be used in a manner so that it is scanned from point to point across and along a given piece of wood or other fibrous material. The results can be entered into a computer programmed to calculate fiber angle at each point sampled. This information can then be reconstructed either to form a video image of the material being scanned or used for other purposes. Gross anomalies, such as knots, bark, cracks, etc. form very different scan patterns which tend to be unique for the type of defect being viewed. The totality of the information generated by the present method now brings accurate automatic grading within the realm of possibility.

It will now be evident to those skilled in the art that many variations could be made from the examples just described without departing from the spirit of the invention. As one example, it is not essential for the photosensors to be located on the same plane or at equiangular positions around the polar axis. Neither is it essential for them to be located in a circular pattern. In some cases it may be beneficial for the photosensors to be clumped together in some areas in order to give expanded resolution in a given range of grain angles. The only requirement that must be met in this case is that one sensor must be located in each quadrant around the polar axis. It is the applicants intention that the invention should be limited only by the scope of the following claims.

What is claimed is:

1. A method of measuring fiber angle in a fibrous material relative to three mutually orthogonal reference axes which comprises:
   a. designating an arbitrary point on the surface of the material as the origin point of the axes;
   b. illuminating an area on the surface of the material including the origin point with an incident beam of light;
   c. sensing the light reflected from the illuminated area using a sufficient number of photosensing means located in space in order to measure the azimuthal angular intensity distribution around the origin point of the reflected light;
   d. determining the azimuthal angular positions of the intensity maxima of the reflected light;
   e. providing an algorithm relating said azimuthal angular positions of the reflected light maxima to the fiber angle; and
   f. calculating the fiber angle relative to all three axes.

2. The method of claim 1 in which said axes are oriented so that one axis projects from the surface into space, said axis being designated as the polar axis, further designating one of the other axes as the reference axis, and estimating the azimuthal angular position of the intensity maxima relative to the reference axis.

3. The method of claim 2 in which the polar axis is essentially normal to the area on the surface being illuminated.

4. The method of claim 2 or 3 in which the photosensing means are located in a plane normal to the polar axis.

5. The method of claim 4 in which the photosensing means include at least four photosensors, with at least one photosensor lying in each quadrant surrounding the polar axis.

6. The method of claim 4 in which the photosensing means includes at least eight photosensors, with at least one photosensor lying in each quadrant surrounding the polar axis.

7. The method of claim 5 in which the photosensors lie at essentially equiangular positions around a circle whose center is located at the polar axis.

8. The method of claim 6 in which the photosensors lie at essentially equiangular positions around a circle whose center is located at the polar axis.

9. The method of claims 2 or 3 in which the incident light beam is along the polar axis.

10. The method of claims 2 or 3 in which the incident light beam is off the polar axis.

11. The method of claim 1 in which the area illuminated has a diameter at least 10 times the average fiber diameter of the substance being measured.

12. The method of claim 1 in which the fibrous material is wood.

13. The method of claim 5 in which the fibrous material is wood.

14. The method of claim 6 in which the fibrous material is wood.

15. The method of claim 5 which further includes normalizing the photosensors to ensure uniform response to a given light level.

16. The method of claim 6 which further includes normalizing the photosensors to ensure uniform response to a given light level.

17. A method of measuring fiber angle in a fibrous material relative to three mutually orthogonal reference axes which comprises:
   a. designating an arbitrary point on the surface of the material as the origin point of the axes, said axes being oriented so that a polar axis projects from the surface into space, and further designating one of the other axes as the reference axis;
   b. locating at least one photosensing means in a position to view the origin point;
   c. sequentially illuminating the origin point with a beam of light from at least one position in each quadrant surrounding the polar axis;
   d. sensing the light reflected from the illuminated origin point with the photosensing means;
   e. determining the azimuthal angular positions, relative to the reference axis, of the light source position or positions which produce maxima in reflected light intensity;
   f. providing an algorithm relating said azimuthal angular light source positions which produce reflected light maxima to the fiber angle measured in relation to the reference axis; and
   g. calculating the fiber angle relative to all three axes.

18. The method of claim 17 in which the polar axis is essentially normal to the area on the surface being illuminated.

19. The method of claims 17 or 18 in which the illumination positions lie in a plane normal to the polar axis.

20. The method of claims 17 or 18 which includes at least eight illumination positions.

21. The method of claim 19 in which the illumination positions lie at essentially equiangular positions around a circle whose center is located at the polar axis.

22. The method of claim 20 in which the illumination positions lie at essentially equiangular positions around a circle whose center is located at the polar axis.

23. The method of claims 17 or 18 in which the photosensing means lies on the polar axis.

24. The method of claims 17 or 18 in which the photosensing means lies off the polar axis.

25. The method of claim 17 in which the illuminated area has a diameter at least 10 times the average fiber diameter of the substance being measured.

26. The method of claims 17 or 18 in which the fibrous material is wood.

27. The method of claim 20 in which the fibrous material is wood.

28. The method of claim 17 which further includes normalizing the light sources to ensure uniform response of the photosensing means to each light source.

29. The method of claim 20 which further includes normalizing the light sources to ensure uniform response of the photosensing means to each light source.

30. A method of measuring fiber angle in a fibrous material relative to three mutually orthogonal reference axes which comprises:
   a. designating an arbitrary point on the surface of the material as the origin point of the axes, said axes being oriented so that a polar axis projects from the surface into space, and further designating a second axis as the reference axis;
   b. locating a plurality of photosensing means in positions to view the origin point;
   c. illuminating the origin point from at least one position in each quadrant surrounding the polar axis, the light from at least one position in each quadrant being essentially monochromatic and of a wavelength different from the light from at least one position in every every other quadrant
   d. directing light reflected from the illuminated area to each photosensing means;
   e. providing filter means so that at least one photosensing means is uniquely sensitive to the wavelength of each illumination source;
   f. measuring the light reflected from the illuminated origin point with the photosensing means;
   g. estimating the azimuthal angular positions, relative to the reference axis, of the point or points or origin which produce a maximum intensity of the reflected light;
   h. providing an algorithm relating said azimuthal angular light source positions which produce reflected light maxima to the fiber angle relative to the reference axis; and
   i. calculating the fiber angle relative to all three axes.

31. The method of claim 30 in which the polar axis is essentially normal to the area on the surface being illuminated.

32. The method of claims 30 or 31 in which the illumination positions lie in a plane normal to the polar axis.

33. The method of claims 30 or 31 which includes at least eight illumination positions.

34. The method of claim 32 in which the illumination positions lie at essentially equiangular positions around a circle whose center is located at the polar axis.

35. The method of claim 33 in which the illumination positions lie at essentially equiangular positions around a circle whose center is located at the polar axis.

36. The method of claims 30 or 31 in which the photosensing means lies on the polar axis.

37. The method of claims 30 or 31 in which the photosensing means lies off the polar axis.

38. The method of claim 30 in which the illuminated area has a diameter at least 10 times the average fiber diameter of the substance being measured.

39. The method of claims 30 or 31 in which the fibrous material is wood.

40. The method of claim 33 in which the fibrous material is wood.

41. The method of claim 30 which further includes normalizing the light sources to ensure uniform response of the photosensing means to each light source.

42. The method of claim 33 which further includes normalizing the light sources to ensure uniform response of the photosensing means to each light source.

43. The method of claim 30 which further includes normalizing the photosensing means to ensure uniform response to each light source.

44. The method of claim 33 which further includes normalizing the photosensing means to ensure uniform response to each light source.

45. The method of claim 30 which further includes beamsplitting means to direct the reflected light to each photosensing means.

* * * * *